United States Patent [19]

Wipf

[11] Patent Number: 4,979,882
[45] Date of Patent: Dec. 25, 1990

[54] SPHERICAL ROTARY MACHINE HAVING SIX ROTARY PISTONS

[75] Inventor: Stefan L. Wipf, Hamburg, Fed. Rep. of Germany

[73] Assignee: Wisconsin Alumni Research Foundation, Madison, Wis.

[21] Appl. No.: 322,675

[22] Filed: Mar. 13, 1989

[51] Int. Cl.[5] .................. F01C 3/02; F01C 17/02; F04B 35/04; A61M 1/10
[52] U.S. Cl. .................... 417/410; 418/186; 418/194; 418/195; 418/196; 128/DIG. 3; 600/16; 623/3
[58] Field of Search ............... 417/410; 418/186, 187, 418/194–196; 600/16; 604/151; 623/3; 128/DIG. 3

[56] References Cited

U.S. PATENT DOCUMENTS

| | | | |
|---|---|---|---|
| 710,756 | 10/1902 | Colbourne | 418/196 |
| 1,332,153 | 2/1920 | Andrews et al. | 418/195 |
| 1,979,368 | 11/1934 | Conklin | 418/188 |
| 2,097,881 | 11/1937 | Hopkins | 418/196 |
| 3,129,460 | 4/1964 | Berger | 418/194 |
| 3,439,654 | 4/1969 | Campbell, Jr. | 418/196 |
| 3,799,126 | 3/1974 | Park | 418/196 |
| 4,021,158 | 5/1977 | Bajulaz | 418/52 |
| 4,324,537 | 4/1982 | Meyman | 418/58 |

FOREIGN PATENT DOCUMENTS

| | | | |
|---|---|---|---|
| 470190 | 7/1978 | U.S.S.R. | 418/195 |

*Primary Examiner*—John J. Vrablik
*Attorney, Agent, or Firm*—Foley & Lardner

[57] ABSTRACT

A spherical rotary machine which may be embodied as a pump, internal combustion engine, compressor or similar other device includes an outer shell with a substantially spherical interior surface, an inner shell including a substantially spherical outer surface centered within the outer shell, and six rotary pistons located between the inner and outer shell. Each piston is rotatable about its own central axis, the six axes being orthogonally centered on the center of the machine. Each piston includes a top convex spherical surface conforming substantially in shape to and located adjacent to the spherical interior surface of the outer shell, a bottom concave spherical surface conforming substantially in shape to and located adjacent to the spherical outer surface of the inner shell, and an oval conical side surface which is substantially defined by lines which are substantially radial with respect to a point near the machine center. The oval side surface of any single piston at least nearly touches tangentially along generally radial lines the oval side surface of each of its four adjacent pistons so that any three pistons which are all adjacent to each other form a displacement chamber which varies in size as the pistons simultaneously rotate. Each piston is operably connected to a gear which is interconnected with the gears of the other pistons to regulate the relative positions of the pistons to ensure that all the pistons rotate with identical speed and direction with respect to the center of the machine. These gears may be located within or without the outer shell of the machine.

45 Claims, 8 Drawing Sheets

SPHERICAL ROTARY MACHINE HAVING SIX ROTARY PISTONS

FIELD OF THE INVENTION

This invention pertains generally to the field of machines having rotary pistons and which may be adapted for use as internal combustion engines, steam engines, compressors, pumps and similar devices, and particularly to those which are spherical in shape.

BACKGROUND OF THE INVENTION

Reciprocating piston engines, pumps and compressors require the conversion of rectilinear motion to circular motiOn or vice versa. As a result, there is energy which is lost and often there is vibration which accompanies the reciprocating motion. Additionally, reciprocating piston-type machines often require a multiplicity of parts such as cam shafts, reciprocating valves, timing gear trains, and other accessories.

Rotating piston machines have been developed which allow for a substantially continuous uniform flow of power. The rotating pistons are often elliptical in shape or are in the shape of rounded equilateral triangles, as disclosed in U.S. Pat. No. 2,097,881 to Hopkins, U.S. Pat. No. 3,439,654 to Campbell, Jr., U.S. Pat. No. 3,799,126 to Park, and U.S. Pat. No. 4,324,537 to Meyman. In these rotary machines, the axes of the rotating pistons are generally parallel to each other so that the pistons utilize space in essentially only two dimensions. As a result, the shape of these types of machines is generally cylindrical or in the form of a rectangular prism.

A spherical piston machine is disclosed in U.S. Pat. No. 4,021,158 to Bajulaz. The machine has a partially spherical chamber wall and a spherical piston mounted within the chamber which includes two elements. Each of the two elements is angularly fixed to a control axle, thereby forming an angle=with a longitudinal axis of the machine. The two elements of the spherical piston are articulated in a zone extending perpendicularly to each control axle. Means are provided for rotatably driving about its own axis at least one of the control axles, as well as for rotatably driving each control axle about the longitudinal axis of the machine. The machine as shown in U.S. Pat. No. 4,021,158 includes a frame structure to support the external gear system which is connected to the machine.

SUMMARY OF THE INVENTION

The spherical rotary machine of the present invention may be embodied as a pump, internal combustion engine, compressor and other similar devices and is particularly suited for application as an artificial heart pump. The preferred spherical rotary machine includes an outer shell with a substantially spherical interior surface, an inner shell including a substantially spherical outer surface centered within the outer shell, and six rotary pistons between the inner and outer shell. Each of the rotary pistons includes a top convex spherical surface conforming substantially in shape to and located adjacent to the spherical interior surface of the outer shell, and a bottom concave spherical surface conforming substantially in shape to and located adjacent to the spherical outer surface of the inner shell. Additionally, each rotary piston includes an oval conical side surface which is substantially defined by lines which are radial with respect to the center of the interior of the outer shell. Each piston is rotatable about its own central axis. The six axes of the six pistons are orthogonally centered on the center of the outer shell interior. The oval side surface of any single piston at least nearly touches tangentially along generally radial lines the oval side surface of each of its four adjacent pistons so that any three pistons which are all adjacent to each other form a displacement chamber which varies in size as the pistons rotate. The machine has eight displacement chambers which are each centered equidistant from the axes of the three adjacent pistons which form a single chamber.

The machine also includes a central core which is centered within the inner shell, and six piston shafts which each extend from the central core into a bearing hole in one piston gear and piston in coaxial relation to the piston central axis. The inner shell has six openings which are each aligned with one piston axis. A piston gear which is coaxially attached to the bottom surface of each piston extends through an opening into the inner shell. Eight connecting gears are rotatably mounted between the central core and inner shell, and between and operably connected to three adjacent piston gears. The rotation of any piston therefore causes all of the pistons to rotate in synchrony at identical angular velocities and directions with respect to the center of the interior of the machine. Alternatively, the gearing which causes the pistons to rotate in synchrony could be external to the outer shell. Such an alternative structure might be preferable if the spherical rotary machine is adapted for use as an engine.

The oval conical side surface of each piston includes two piston ends which are 180° apart with respect to the central axis of the piston, and which are each inclined at approximately a 54.7356° angle to the central axis of the piston. At about 90° from each piston end with respect to the central axis of the piston, the oval conical surface is inclined at approximately a 35.2644° angle to the central axis of the piston. Preferably, the oval conical side surface of each piston includes two opposed approximately elliptical conical surface sections which are each centered at about 90° from both ends with respect to the central axis. In the heart pump embodiment of the invention, the oval conical side surface of each piston further includes two cylindrical surface sections at the ends of the piston which intersect the two opposed elliptical conical surface sections.

Four of the rotary pistons, which are denoted herein as equatorial pistons, each have a cavity extending radially inwardly from a top of the piston which is formed concentric with respect to the central axis of the piston. A motor may be located within the cavity of each equatorial piston where the machine is acting as a self contained pump, for example, an artificial heart pump. The outer shell has four openings which are located over these cavities, and includes four covers which fit over to close the openings. Each motor is preferably mounted to one of these covers. Several gears are utilized for directing rotational motion from each motor to the adjacent piston.

Two of the rotary pistons, which are denoted herein as polar pistons, each have an inlet passage forming an inlet orifice in the top convex spherical surface of the piston, and a set of inlet apertures opening near the end of each elliptical conical surface section such that as the piston rotates, each inlet aperture faces into a displacement chamber which is increasing in size. Similarly, each polar piston also has an outlet passage forming an outlet orifice in the top convex spherical surface of the piston, and a set of outlet apertures opening near the other end of each elliptical conical surface section, so that as the piston rotates, each outlet aperture faces toward a displacement chamber which is decreasing in size.

The spherical rotary machine may be embodied so as to be spherical in outside configuration. Additionally, fluids may be moved separately through the upper and lower halves of the machine, in its embodiment as a pump, in such a manner that the fluids do not mix. For each full rotation of the pistons, the spherical rotary machine can discharge four pulses of fluid which are each equal to twice the volume of a single open displacement chamber. Accordingly, the total displacement per one full rotation of the pistons is about 120% of the volume within the pump.

Further objects, features, and advantages of the invention will be apparent from the following detailed description taken in conjunction with the accompanying drawings.

DESCRIPTION OF THE PREFERRED EMBODIMENT

Figure 1:
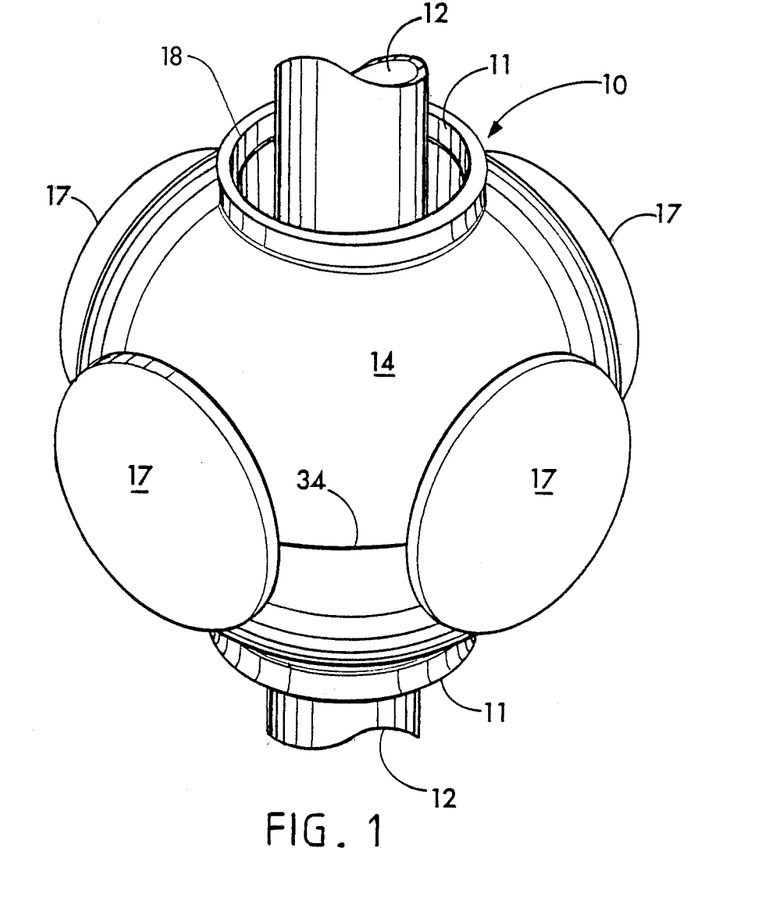
FIG. 1 is a perspective view of the preferred spherical rotary machine embodied as a pump.
Figure 5:
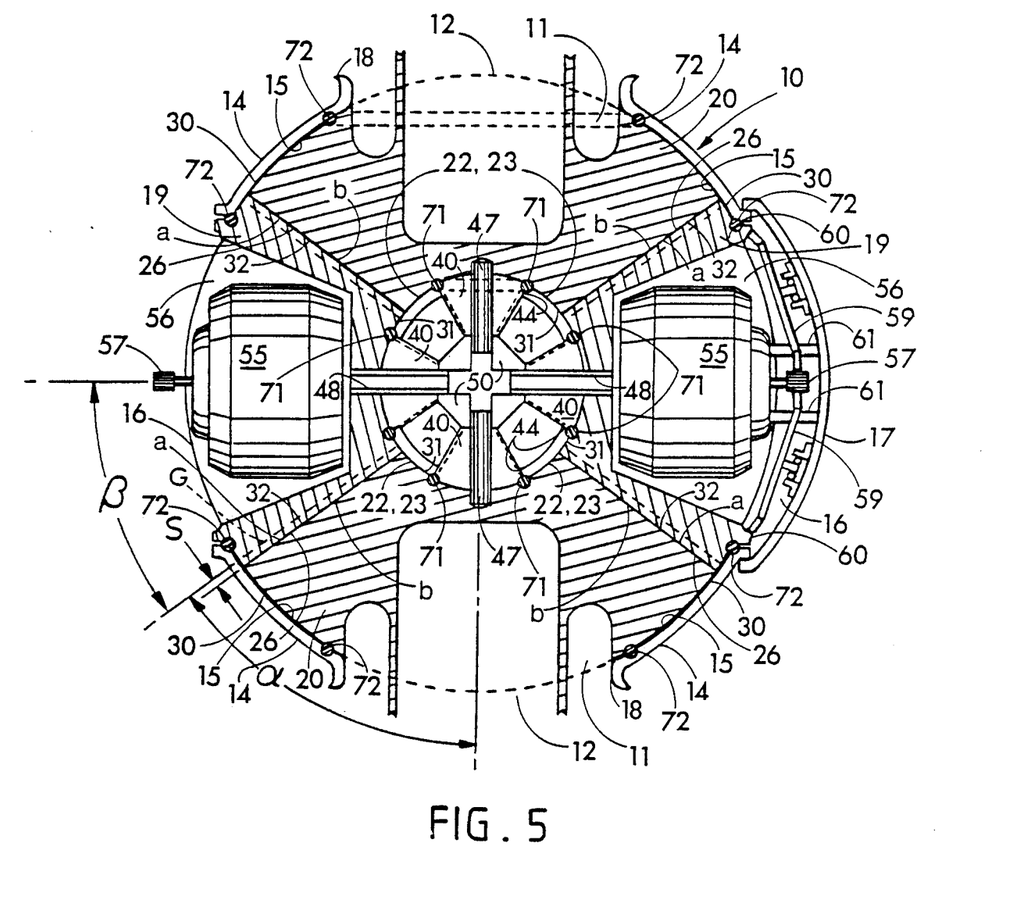
FIG. 5 is a cross-sectional view of the spherical rotary machine through the axes of the polar pistons and of two of the equatorial pistons. The relative position of the pistons is as illustrated in FIG. 3.
Figure 6:
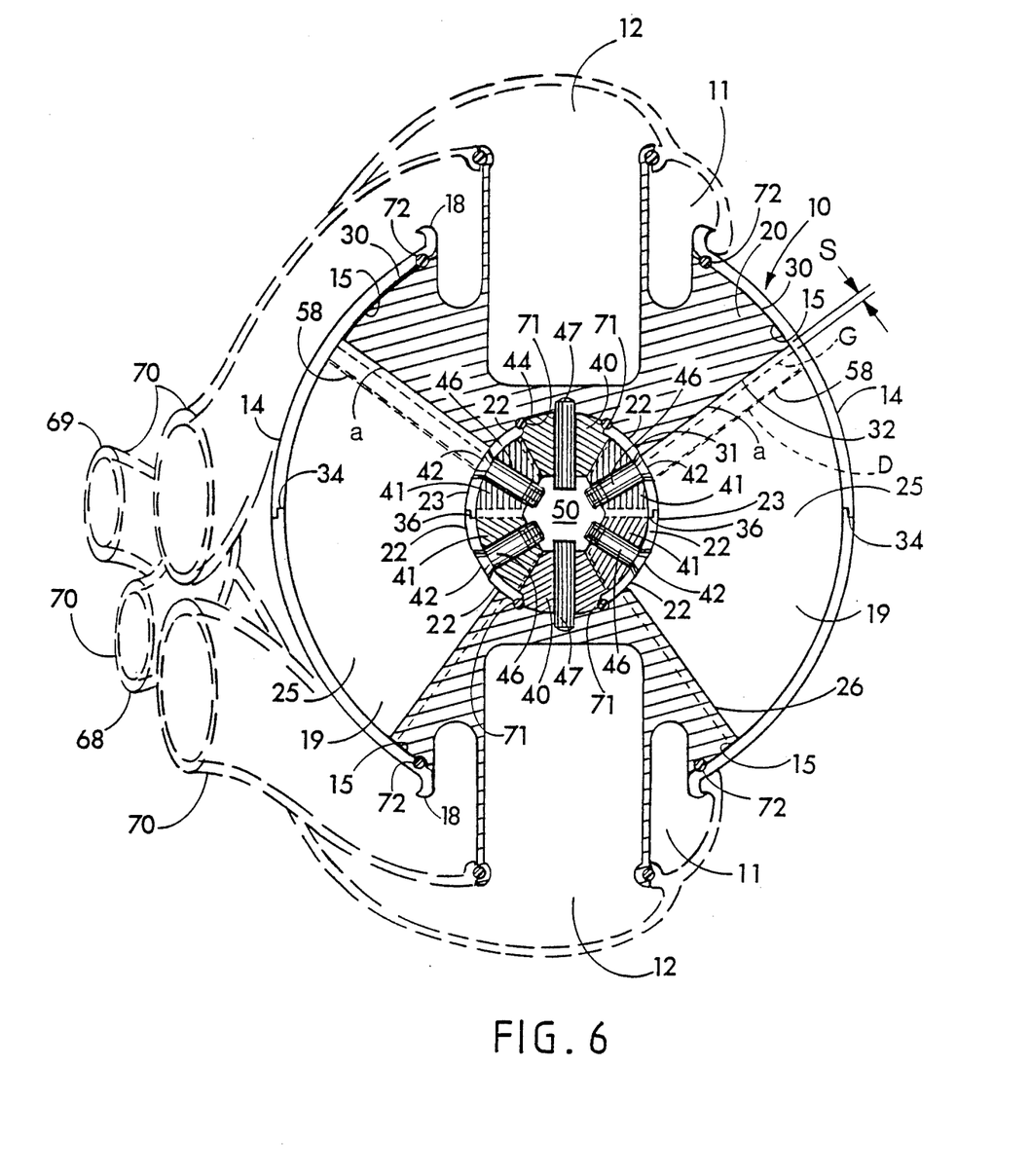
FIG. 6 is a cross-sectional view of the spherical rotary machine through the axes of the polar pistons in a plane 45° to the axes of the equatorial pistons as illustrated in FIG. 4 with the pistons rotated 45° from the positions shown in FIG. 5.

With reference to the drawings, a spherical rotary machine in accordance with the invention is shown generally at 10 in FIG. 1. As shown, the preferred spherical rotary machine 10 is a heart pump with two inlet orifices 11 for receiving blood and two outlet orifices 12 through which blood leaves the machine 10. The machine 10 includes and is enclosed by an outer shell 14 with a substantially spherical interior surface 15, as best shown in FIGS. 5 and 6. The outer shell 14 includes four access openings 16, four piston covers 17 which cover and close the access openings 16, and two fluid transfer openings 18 through which the inlet and outlet orifices 11 and 12 open. As shown schematically in FIGS. 2–4, the machine 10 includes six identically shaped rotary pistons 19 and 20 of two-fold symmetry underneath the outer shell 14. Beneath the pistons 19 and 20 is an inner shell 22 having a substantially spherical outer surface 23 which is spherically concentric with the interior surface 15 of the outer shell 14. Thus the pistons 19 or 20 are located between two concentric spherical surfaces 15 and 23, and are pair-wise oppositely positioned on three orthogonal axes going through the center of the interior of the machine 10.

Figures 2, 3, 4:
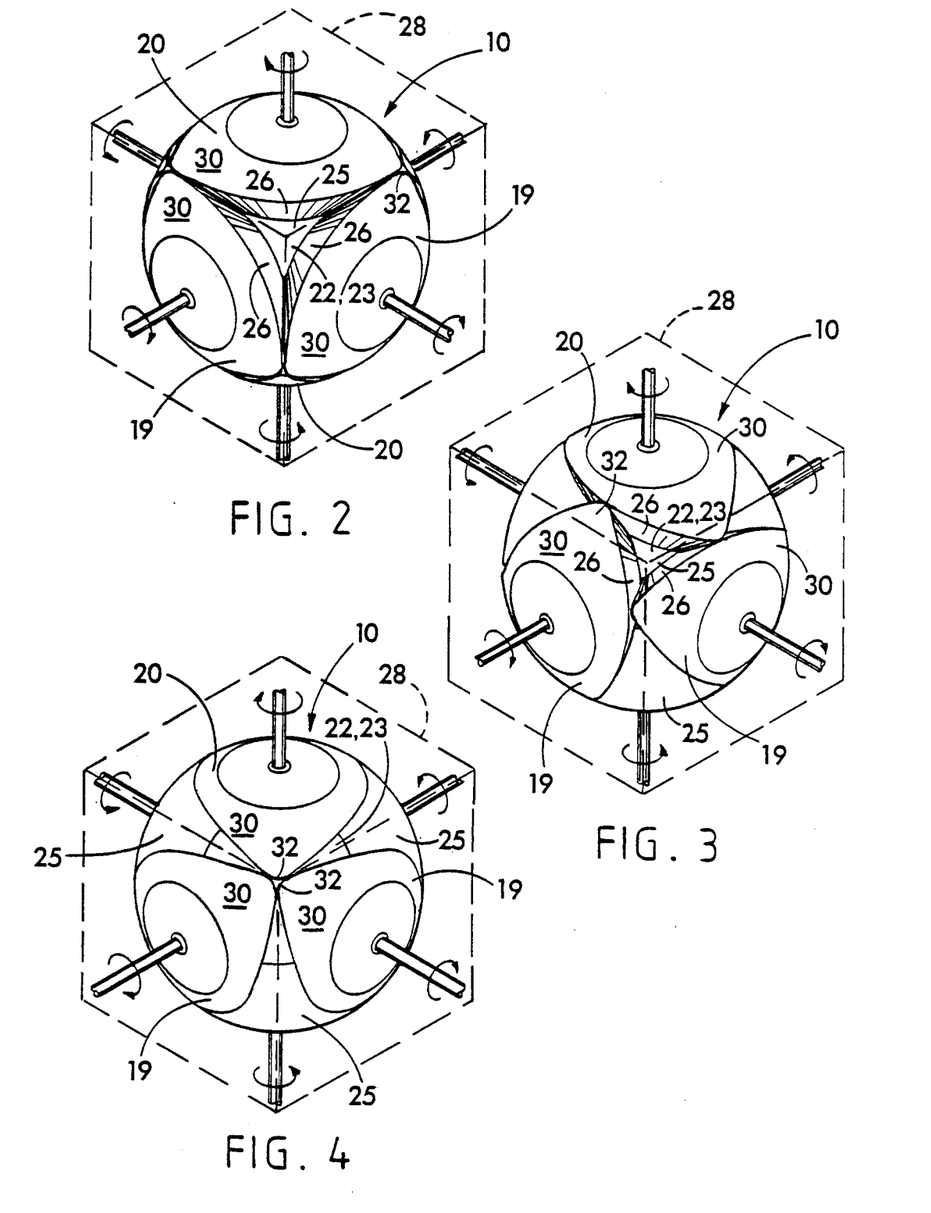
FIG. 2 is a schematic perspective view of the spherical rotary machine with its outer shell removed, looking directly at a fully open displacement chamber, with the pump placed within an analogous cube shown in dashed lines. Shafts are shown extending out of the pistons as an alternative means of connecting the pistons to gears which might interconnect the pistons.
FIG. 3 is a schematic perspective view of a spherical rotary machine with its outer shell removed, looking directly at a half open, half closed displacement chamber, turned at 45° from the view of FIG. 2.
FIG. 4 is a schematic perspective view of a spherical rotary machine with its outer shell removed, looking directly at a closed displacement chamber.

The six pistons are geared, with the gears placed inside the inner shell 22 as shown in FIGS. 5 and 6, or outside the outer shell 14 as the external shafts allow for in FIGS. 2–4, so that all six pistons rotate at the same speed with the same sense of rotation. Between the six pistons are eight spaces forming positive displacement chambers 25 which pulsate between a minimum and a maximum volume during rotation of the pistons 19 and 20. Each displacement chamber 25 is formed by the spherical interior surface 15 and the spherical outer surface 23 and by the oval conical side surfaces 26 of three adjacent rotary pistons 19 or 20 which touch or nearly touch each other tangentially at all times during rotation. The term "at least nearly touch" is used sometimes instead of the word "touch" due to the fact that, in a heart pump, the material forming the pistons 19 or 20 themselves might not actually touch. In a heart pump, the pistons 19 or 20 preferably would have a bio-coating with roughened surface, and a double layer called the Endothelial lining or Intima which is formed by the blood itself. A more detailed description of these layers is given below.

The oval conical side surface 26 of each piston 19 or 20 is formed substantially from oval cones which are truncated by the spherical interior surface 15 and the spherical outer surface 23, with their theoretical apex at, or near, the center of the spherical surfaces 15 and 23. The oval cones are determined by the condition that during rotation, each piston 19 or 20 has to touch or nearly touch tangentially all of its neighboring pistons 19 and 20 all of the time. However, the degree of elongation of the oval cross section can be chosen between the two extremes of an almond shape with two sharp ends, and a circle. The extreme case of the almond shape results in a minimum displacement volume of zero, therefore causing a maximum positive displacement action. The other extreme of a circle results in a constant sized displacement chamber between the pistons 19 or 20, so that there is no positive displacement action at all. The preferred choice is close to the almond shape, thereby giving large displacement action, yet avoiding sharp ends to have the end surfaces touching each other tangentially for better sealing therebetween. FIGS. 2-4 show a spherical rotary machine 10 with the outer shell 14 removed, looking directly at a single displacement chamber 25. As shown in FIG. 2, the displacement chamber 25 is opened to its maximum size. In FIG. 3, the displacement chamber 25 is opened to an intermediate size. In FIG. 4, the displacement chamber 25 is at its minimum size. As shown, the positions of the pistons 19 or 20 are analogous to the faces of the cube 28 shown in dashed lines, and the displacement chambers 25 are positioned analogously to the corners of the cube 28.

The four pistons 19 are called equatorial pistons, and have coplanar central axes positioned within an equatorial plane. The other two pistons 20 are called polar pistons, and have a common vertical axis. Of the eight displacement chambers 25, four are positioned substantially above the equatorial plane and four substantially below. All six pistons 19 and 20 have substantially identical outer shapes but are formed differently internally to perform different functions. Each piston 19 or 20 includes a top convex spherical surface 30 which conforms substantially in shape to and is located adjacent to the spherical interior surface 14 of the outer shell 14. The pistons 19 or 20 also each include the oval conical side surface 26 which is substantially defined by line segments which are substantially radial with respect to a point near the center of the machine 10. Each piston 19 or 20 includes a bottom concave spherical surface 31 which conforms substantially in shape to and is located adjacent to the spherical outer surface 23 of the inner shell 22, thereby causing the oval conical side surface 26 of each piston 19 or 20 to be truncated. The inlet and outlet orifices 11 and 12 open from the top convex spherical surfaces 30 of the polar pistons 20 through the outer shell 14.

Each piston 19 or 20 is rotatable about its own central axis. As shown in FIGS. 2-4, the six axes are orthogonally centered on the center of the interior. As the pistons 19 or 20 rotate, the oval side surface 26 of each piston 19 or 20 substantially touches or nearly touches tangentially, along generally radial line segments, the oval side surface 26 of each of its four adjacent pistons 19 or 20, such that any three pistons 19 or 20 which are all adjacent to each other and which form a displacement chamber 25 therebetween, have substantially identical portions of their oval side surfaces 26 which are defined by the generally radial line segments. In other words, the portions of each piston 19 or 20 which form a single displacement chamber 25 are always identical, and they simultaneously change as the chamber 25 changes in size. The substantially identical portions of the oval side surfaces 26 of three neighboring pistons 19 or 20 thus actually define the displacement chamber 25 which upon rotation of the pistons 19 or 20 varies in size from a minimum size to a maximum size. Each displacement chamber 25 is centered equidistantly from the axes of the three adjacent pistons 19 or 20 which form the single chamber 25.

Figure 12:
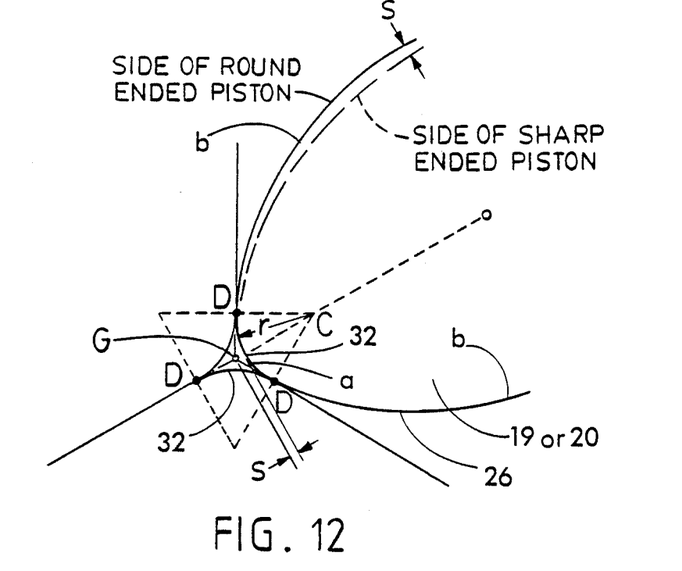
FIG. 12 is a schematic view of one end of a piston, demonstrating the geometrical considerations for that piston.

As illustrated in FIG. 5, a crucial angle in the construction of the machine 10 is the angle $\alpha$ between the body diagonal of a cube and an edge of a cube, that is $\alpha = 54.7356°$. An equally important angle is the angle $\beta$ which is equal to $35.2644°$, the complement of $\alpha$. Referring to FIG. 12, in the extreme case of a sharp-ended piston, each piston 19 or 20 would touch the oval conical side surface 26 of a neighboring piston 19 or 20 always along a line which is inclined at $54.7356°$ to the central axis of the piston 19 or 20. In FIG. 12, such a line would be represented by a line vertical to the plane of the drawing through the point G which also shows where all three sharp-ended pistons would touch if the displacement chamber were closed.

However, in the preferred piston 19 or 20, the two ends 32, which are about 180° apart with respect to the axis, are rounded. The piston A in FIG. 11 may be a polar piston 20, while pistons B, C and the other two not shown, may be the four equatorial pistons 19. The displacement chamber formed by the pistons A, B and C is closed. As shown in both FIGS. 11 and 12, the rounded ends 32 of the pistons 19 or 20, in closed position, therefore touch another piston 19 or 20 in a line D which extends generally upwardly out of FIGS. 11 and 12. The lines D divide the oval conical side surface 26 of the round ended pistons 19 or 20 into four sections which are designated $a_I$, $a_{II}$, $b_I$, and $b_{II}$ on the schematic pistons A, B and C in FIG. 11. The sections a are circular and represent cylindrical surface sections a. On the other hand, the sections b are opposed elliptical conical surface sections b. The term "elliptical" is used broadly to include other curves which are similar or approximate in appearance to elliptical curves. During rotation, points of any section a touch only points of section b of the neighboring piston 19 or 20. In fact, each point from section a touches only a specific point from section b. Again, the terminology "point" as used with reference to schematic FIGS. 11-12 actually refers to lines which extend upwardly from the figure. Thus, to each point of section $a_{IA}$ on piston A there corresponds a point on section $b_{IC}$ of piston C and on $b_{IB}$ of piston B and two more points on the other two neighboring pistons 19 or 20 not shown in FIG. 11. Similarly, points in sections $a_{IIA}$ correspond with points in sections $b_{IIB}$ and $b_{IIC}$. Consequently, the section a curves generate the section b curves of the adjacent pistons, and vice versa.

A fabricator of these pistons 19 or 20 has some freedom in the choice of curves a or b. In the extreme case of the sharp-edged piston, the two a sections in FIG. 11 each degenerate into a point, actually a line G. In the other extreme case of pistons with a circular cross-section, the conical side surface 26 of each piston degenerates to a right circular cone.

Figures 9, 10, 11:
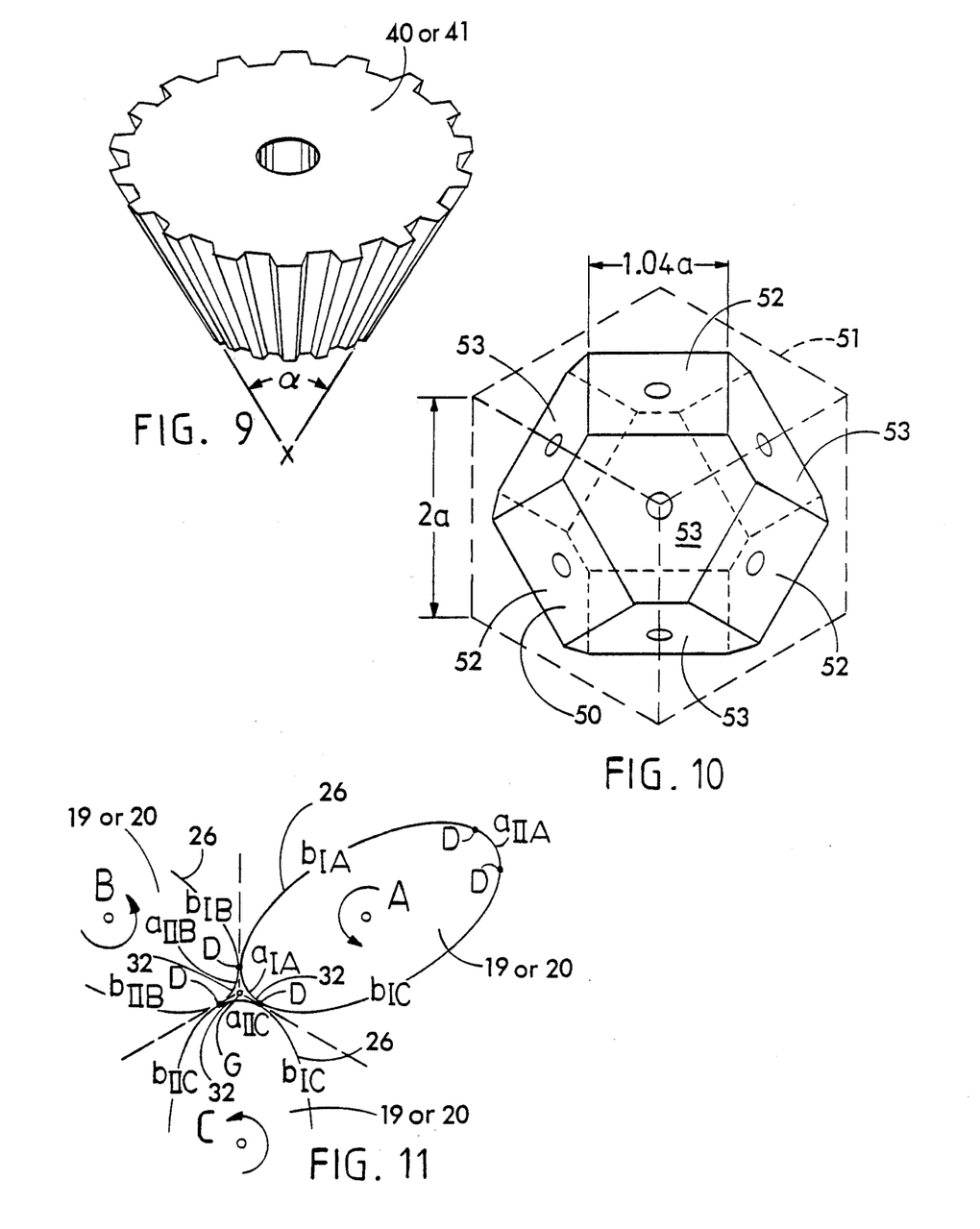
FIG. 9 is a perspective view of a gear which may function as a piston gear or a connecting gear.
FIG. 10 is an illustrative perspective view of the central core.
FIG. 11 is a schematic view showing three pistons forming a displacement chamber therebetween which is closed, and illustrating the two opposed elliptical conical surface sections and two cylindrical surface sections on each piston.

Because of ease of fabrication, it may be practical to choose the form of section a as part of a circular cylinder. As shown in FIGS. 11 and 12, the sections a which form the ends 32 of the pistons 19 or 20 are shown at the cross-section to have a radius r with center C. Using a larger r results in the advantages of better tangential seals and easier manufacturing of the pistons, but the disadvantage of smaller pump displacement. The reduction of pump displacement can be gauged in FIG. 12 from the displacement $S = 0.1547r$. In the preferred machine 10, r is chosen to be 6.35 mm so that $S = 0.982$ mm as seen in FIGS. 5 and 6.

Again, a sharp ended piston would have an oval conical side surface with ends which are formed at the angle $\alpha = 54.7356°$ to the central axis of the piston 19 or 20.

For example, if the pistons 20 shown in FIGS. 5 and 6 were sharp ended, their ends would extend to the dashed line G which forms the angle α with the central axis of the pistons 20. Similarly, sharp ended pistons have an oval conical surface which at 90° from either end with respect to the central axis is inclined at an angle $\beta = 35.2644°$ to the central axis of the piston 19 or 20. Thus, in FIGS. 5 and 6, the dashed line G also shows how far the oval conical surface of a sharp ended piston would extend at about 90° from ether end of the piston 19. As shown, the dashed line G forms the angle $\beta = 35.2644°$ to the central axis of the piston 19 in FIG. 5.

Since the preferred pistons 19 and 20 are not sharp ended, but instead have rounded ends 32, the pistons 19 and 20 actually touch each other along the solid line at 32 in FIG. 5 instead of the dashed line G. Therefore the angle which the end 32 of a piston 19 or 20 forms with the central axis is still 54.7356° but shifted by the distance S as shown in FIG. 6, and illustrated in FIG. 12. Similarly, the angle which the oval conical surface 26 forms at about 90° from either end 32 is still a 35.2644° angle to the central axis of the piston 19 or 20 but shifted by the distance S.

Thus as shown in FIGS. 5, 6, 11 and 12, the preferred spherical rotary machine 10 has pistons 19 and 20 which each have an oval conical side surface 26 which includes two opposed elliptical conical surface sections b which are each centered at about 90° from both ends 32 with respect to the central axis. Additionally, the oval conical side surface 26 of each piston 19 or 20 further includes two cylindrical surface sections a at the ends 32 of each piston which intersect the two opposed elliptical conical surface sections b, which also extend between the cylindrical surface' sections a. The two cylindrical surface sections a of each piston 19 or 20 touch or at least nearly touch only the elliptical conical surface section b of other pistons 19 or 20 as the pistons rotate.

FIG. 5 shows a cross-sectional view through the axes of the polar pistons 19 or 20 and two of the equatorial pistons 19. The positions of the pistons 19 and 20 is such that all of the displacement chambers 25 are of equal size, that is they are half-open and half-closed as illustrated in FIG. 3. The equatorial pistons 19 are sectioned through their narrowest part, and the polar pistons 20 through their widest part. Since the pistons 19 and 20 have rounded ends 32, the pistons 19 and 20 touch in a line 32 shifted by about 1 mm from the dashed line G. Aqain, if the pistons 19 and 20 had sharp ends, the pistons 19 and 20 would touch along the lines G.

FIG. 6 shows a cross-sectional view through the axes of the polar pistons 20 in a plane 45° to the axes of the equatorial pistons 19, i.e., through the centers of the displacement chambers 25, a position of the pistons illustrated in FIG. 4. Additionally, the pistons 19 and 20 shown in FIG. 6 are rotated by 45° from the positions shown in FIG. 5. The widest section of the upper polar piston 20 is again shown. The double dotted lines 58 indicate where each pair of equatorial pistons 19 touch each other in the plane of the section, to form the substantially closed displacement chambers 25 near the ends 32 of the upper polar piston 20 and the open displacement chambers 25 below the double dotted lines 58. The narrowest section of the lower polar piston 20 is shown in FIG. 6. Adjacent to the lower polar piston 20 are the two open displacement chambers 25 which extend upwardly to the double dotted lines 58.

Figure 7:
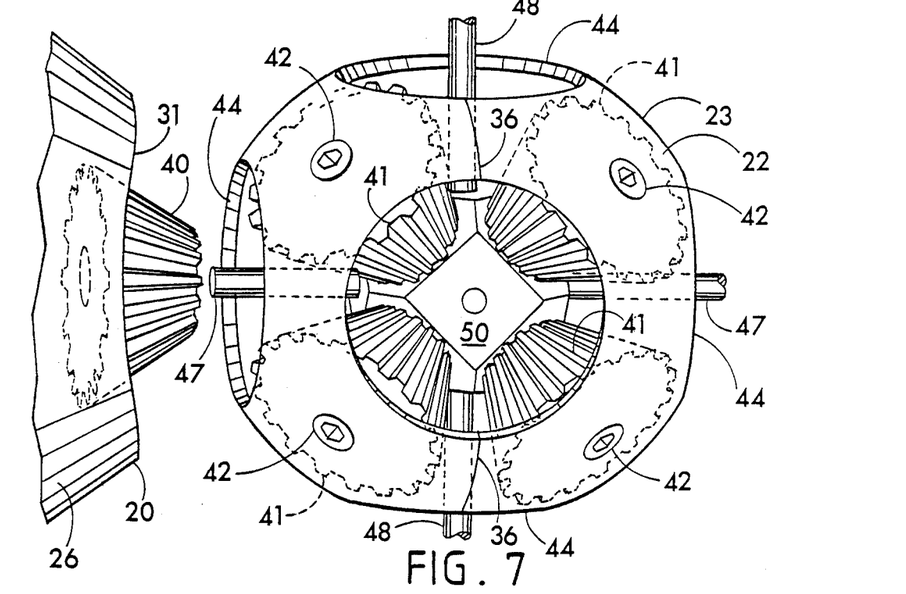
FIG. 7 is a perspective view of the inner shell with the gears and central core therein and a piston with its piston gear spaced away from the inner shell.
Figure 8:
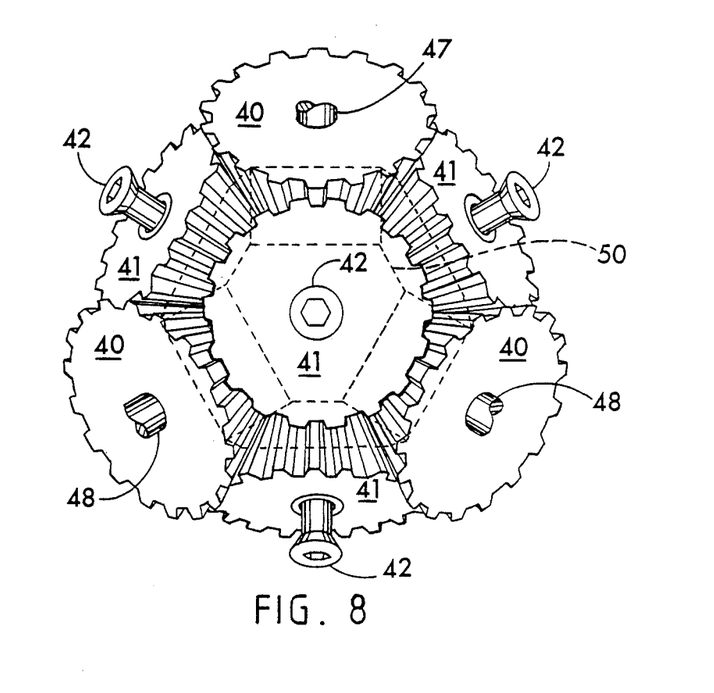
FIG. 8 is a perspective view illustrating the manner in which the piston gears and connecting gears mesh together within the inner shell.

In the embodiment of the machine 10 as a heart pump, the outer shell 14 has an exemplary inside diameter of 108 mm (8.5 inch) and a wall thickness of 2.5 to 3 mm. The upper half of the outer shell 14 may be made a little thicker than the lower half because it replaces the left ventricle, and must withstand a pressure differential of 120 mm Hg., six times higher than the pressure differential in the lower half of the outer shell 14 which serves as a right ventricle. The two hemispheres join at the equator 34 in tongue and groove joints as shown in FIG. 6, and are held together by the piston covers 17 which preferably are screwed on as shown in FIGS. 1 and 5. In the embodiment of the machine 10 as a heart pump, the inner shell 22 has an exemplary outside diameter of 38 mm (1.5 inch) and a wall thickness of approximately 2 mm (80 mils). It is formed of two halves which have blood-tight tongue and groove joints around the equator 6, as shown in FIGS. 6 and 7. The inner shell 22 serves as a gear box which contains the six piston gears 40, eight connecting gears 41 and a central core 50 which are shown in FIGS. 5-9. In FIG. 6, four of the eight connecting gears 41 are shown in section. The other four connecting gears 41 lie pairwise above and below the plane of the drawing comprising FIG. 6. The inner shell 22 is held together by the bolts 42 through the connecting gear axles 46 for the eight connecting bevel gears 41 which are best shown in FIGS. 7 and 8. The bolt heads are located at the centers of the displacement chambers 25 and therefore should be bio-coated or should be formed from a biocompatible material.

The gears 40 and 41 keep all of the pistons 19 and 20 turning with the correct relative phase and transmit the power from four directly driven equatorial pistons 19 to the two polar pistons 20. The gears 40 and 41 and appurtenant structures comprise means for causing the pistons 19 and 20 to rotate at identical angular velocities and directions with respect to the center of the machine 10. The gearing therefore causes all of the pistons to rotate in synchrony. The six piston gears 40 are affixed to the bottom concave spherical surface 31 of each piston 19 and 20 so as to be coaxial with each piston. The inner shell 23 has six openings 44 which are each aligned with one piston 19 or 20 axis. When the pistons 19 and 20 are in place around the inner shell 22, the piston gears 40 extend through the openings 44 into the inner shell 22, as shown in FIGS. 5, 6, and 7. Each piston gear 40 thereby symmetrically engages four adjacent connecting gears 41, and each connecting gear 41 symmetrically engages three adjacent piston gears 40 as shown in FIGS. 5-8. The piston gears 40 do not engage other piston gears 40, and the connecting gears 41 do not engage other connecting gears 41. Each equatorial piston 19 and attached gear 40 are placed on hollow axles 48, and each polar piston 20 and attached gear 40 are positioned on axles 47, which are fixed in the central core 50, along with the connecting gear 41 axles 46.

As shown in FIG. 10, for the pump dimensions given above, the central core 50 is formed within a cube 51 with dimensions side exemplary 2a=16 mm. The eight corners of the cube 51 are cut away normally to the body diagonal at a distance a = 8 mm from the center of the cube 51. This leaves six square sections 52 remaining in the middle of the original cube 51 side surfaces The length of a side of each square section 52 is 8.28 mm, or 1.04a. The eight faces 53, formed by cutting the corners of the cube 51 away, have the shape of truncated equilateral triangles with height 9.8 mm=1.23a. The central core 50 is centered within both the machine interior and within the inner shell 22. Each of the six piston axles 47 and 48 extend from the central core 50 into bearing holes in the piston gears 40 and pistons 19 and 20 in coaxial relation to the piston central axis.

The eight connecting gears 41 are rotatably mounted between the central core 50 and inner shell 22, and also between and operably connected to three adjacent piston gears 40 so that the rotation of any single piston 19 or 20 causes the rotation of all pistons 19 and 20. Both the piston gears 40 and the connecting gears 41 should have a number of teeth N which is a multiple of 6. For smoother operation, it is preferable to have N be an odd multiple of the number 6 in order to have alternating positive and negative engagement at the four places of engagement for a piston gear 40 with the adjacent connecting gears 41. In the embodiments of the gears 40 and 41 shown herein, $N=3*6$ and thus each gear 40 or 41 has 18 teeth, as is best shown in FIGS. 8 and 9. The opening angle of each gear 40 or 41 is equal to $\alpha = 54.7356°$. Thus the gear teeth are inclined at about a 27.3678° angle to the axis of the gear 40 or 41. Such gears generally have to be cut specially. It is worth noting that the smaller of a 1:2 meter gear pair has an opening angle of 53.13°, which differs by only 1.6° from the correct angle. This gear is already available and might be practical to use in appropriate applications.

The pistons 19 and 20 are driven by four mOtors 55 (e.g., small DC electric motors) which are located within cavities 56 in the equatorial pistons 19. The cavities 56 are located radially inward from the access openings 16. Each equatorial piston 19 has one cavity 56 which extends radially inwardly from the top of the piston 19, and which is concentric to the piston's central axis. Each motor 55, which is located within one cavity 56, is mounted to one piston cover 17 as shown at 61 in FIG. 5. The total power needed to drive the exemplary heart pump machine 10 having the dimensions set forth above can be less than four watts. Each motor preferably should be capable of having an output of about 1.5 watts. The motors 55 have a small gear 57 which is operably connected to drive two spur gears 59 which are mounted within bearings to the piston cover 17. Around the periphery of the piston cavity 56 is an inside ring gear 60 which is operably connected to and driven by the spur gears 59. The small gear 57 has about a 3 mm diameter, and the inside ring gear 60 has about a 50 mm diameter. Thus there is a 16:1 gear reduction achieved. For a pulse rate of 40 to 120 per minute (10-30 piston RPM) the motor turns at 160-480 RPM. Motors with a higher rotational velocity would need additional or different reducing gears. Electrical connections between the four motors 55 may be made through the hollow axles 48 by way of the central core 50 to avoid four separate leads through the outer shell 14. Since the motors 55 are mounted to the piston covers 17, the motors 55 may be removed from the cavities 56 by simply removing the covers 17. Placing the covers 17 over the access openings 16 also closes the cavities 56.

Figure 15:
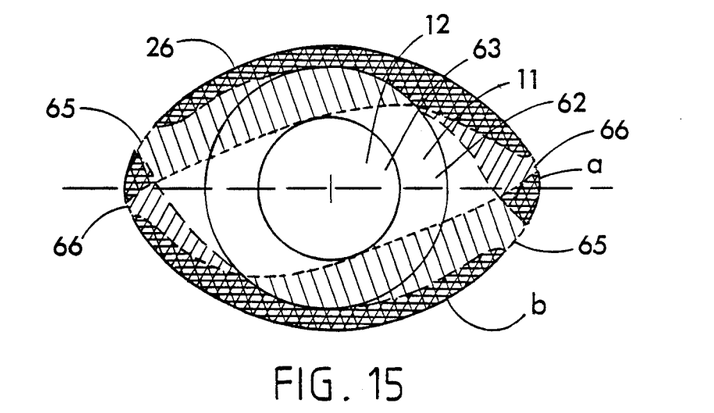
FIG. 15 is a horizontal cross-sectional view of a piston showing the inlet and outlet passages.
Figure 16:
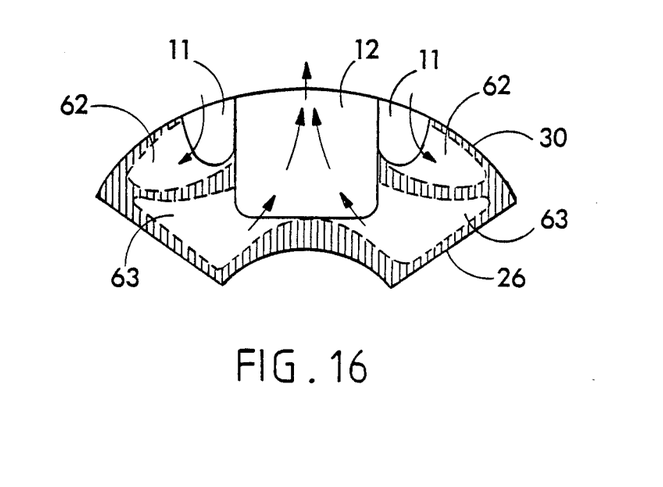
FIG. 16 is a longitudinal cross-sectional view of a piston showing the inlet and outlet passages.

The polar pistons 20 have inlet and outlet passages 62 and 63 which are best shown in FIGS. 15 and 16. The inlet passage 62 forms the ring-shaped inlet orifice 11 which is concentric with respect to the central axis of the piston 20, and a pair of inlet apertures 65 which open in each elliptical conical surface section b near one end 32 such that as the piston 20 rotates, each inlet aperture 65 lags with respect to the adjacent end 32. The outlet passage 63 forms the circular outlet orifice 12 in the top convex spherical surface 30 of the piston 20. The outlet orifice 11 is circular and concentric with respect to the central axis of the piston 20. The outlet passage 63 also forms a set of outlet apertures 66 which open in each cylindrical surface section a, near one end 32 of the piston 20, such that as the piston 20 rotates counterclockwise, each outlet aperture 66 leads with respect to the adjacent end 32. The inlet apertures 65 are located in the elliptical conical surface sections b, while the outlet apertures 66 are located within the cylindrical surface section a, so that the inlet apertures 65 and outlet apertures 66 never open both at the same time into the same displacement chamber 25. The inlet apertures 65 face expanding chambers 25 while the outlet apertures 66 face shrinking chambers 25. Thus regurgitation of blood, or blood flowing back from the aorta to the mitral atrium is avoided. Note that the inlet passages 62 and the outlet passages 63 are not shown in their entirety in FIG. 5.

The exemplary inlet apertures 65 are 30 mm long and 5 mm wide, giving a throughput area of 1.5 cm$^2$. Thus, two inlet apertures 65 together would have an opening of 3 cm$^2$. This is about 30% of the cross-section of the mitral passaqe (approximately 34 mm diameter) and compares with the opening of the mitral valve in the open state. The outlet aperture 66 is 30 mm long and 3.5 mm wide giving a cross-section of 1 cm$^2$ and a total area of 2 cm$^2$ for two apertures 66. Again, this is about 30% of the cross-section of the aorta (about 28 mm diameter). Inside the pistons 20, the passages 62 and 63 widen and connect the inlet and outlet apertures 65 and 66. Thus, the inlet apertures 65 open into chambers 25 which are expanding, and the outlet apertures 66 open into chambers 25 which are closing. The upper polar piston 20 serves the four displacement chambers 25 located substantially above the equator, while the lower polar piston 20 serves those chambers 25 below the equator.

Note that the displacement chambers above the equator 34 do not communicate with those chambers 25 below the equator. The upper and lower chambers 25 are always separated by the four equatorial pistons 19. Therefore, the upper half of the machine 10 can be given the function of one heart ventricle, say the left ventricle, and the lower half of the machine that of the right ventricle. Thus, the upper polar piston 20 replaces the mitral valve and feeds into the aorta connection 68, and the lower polar piston 20 replaces the tricuspid valve and feeds into the pulmonary artery connection 69. Both the upper and lower halves of the machine 10 discharge equal volumes per pulse.

The machine 10 also includes six small O-rings 71 and six large O-rings 72. As shown in FIGS. 5 and 6, each of the six small O-rings 71 is positioned between the outer surface 23 of the inner shell 22 and the bottom concave spherical surface 31 of one piston 19 or 20. The O-rings 71 are positioned to be concentric to the central axis of the piston 19 or 20. Fluid within the interior of the machine is thereby substantially prevented from' leaking into the openings 44. Four large O-rings 72 are each positioned between the top convex spherical surface 30 of one equatorial piston 19 concentrically outside of the cavity 56 with respect to the piston 19 central axis, and the spherical interior surface 15 of the outer shell 14. Fluid within the interior of the machine 10 is thereby substantially prevented from leaking into the cavities within the equatorial pistons 19. The two remaining large O-rings 72 are each positioned between the top convex spherical surface 15 of each polar piston 20 concentrically outside of the ring-shaped inlet opening 11 with respect to the central axis of the piston 20, and the spherical interior surface 15 of the outer shell 14. Therefore, fluid within the inlet orifice is substantially prevented from leaking into the interior of the machine 10 between the piston 20 and the outer shell 14.

The O-rings 71 and 72 function to form seals against leakage of blood which allow for rotation of the pistons 19 and 20. Preferably, the O-rings are made from tetrafluoroethylene resins, such as those sold under the trademark "Teflon". The O-rings fit into precisely machined grooves within one or more of the surfaces between which the O-rings lie. For application as a blood pump, the grooves may be bio-coated, as explained below, to reduce hemolysis. The O-rings 71 and 72 and appurtenant structure as shown in FIGS. 5 and 6 are not meant to be an exact section view of these components.

Figure 13:
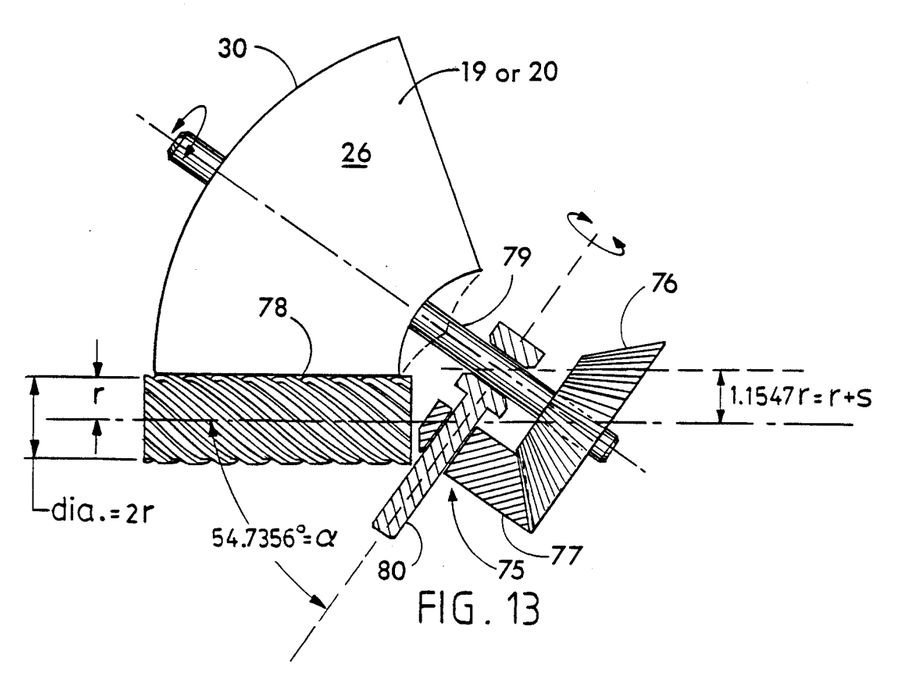
FIG. 13 is a side elevation view of a device which may be utilized in manufacturing the pistons.

In machining the pistons 19 and 20, it must be kept in mind that the sections b are generated with the sections a of the oval conical side surface 26 and vice versa. As shown in FIG. 13, a special cutting device 75, which includes two 45° bevel gears 76 and 77, can position and lead a piston 19 or 20 past a cylindrical milling tool 78. The milling tool 78 will cut one elliptical conical surface section b of a piston 19 or 20 which is fixed to the mounting axle 79. For machining the other elliptical conical surface section b, the positioning axle 80 is lifted to disengage the gears 76 and 77, and turned by 180°. The gears 76 and 77 should have an even number of teeth.

Figure 14:
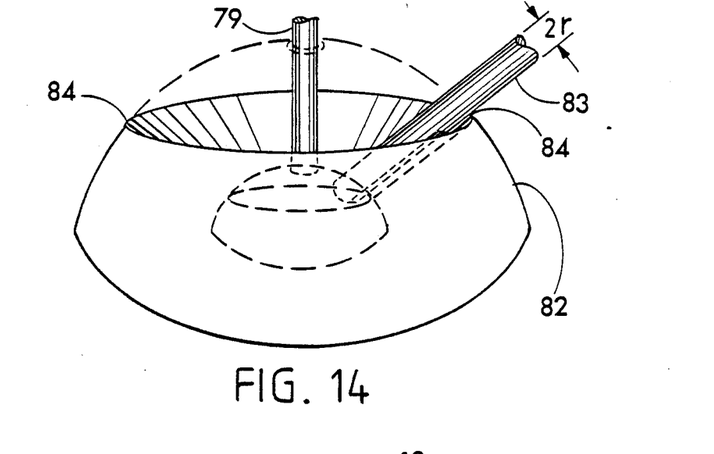
FIG. 14 is a perspective view of a negative mold which may be utilized to aid in manufacturing the pistons.

The resulting piston 19 or 20 has only elliptical conical surface sections b which join at sharp ends. Nevertheless, the sharp ended piston may be a master from which to make a negative mold 82, as shown in FIG. 14. The cylindrical surface sections a for the negative mold 82 may be made by inserting cylinders 83 of radius r into the two sharp ends of the mold 82 and filling in the small space between the cylinder 83 and the sharp end 84 with mold material. The passages 62 and 63 inside the pistons 19 and 20 may be manufactured, by molding in clay or some other suitable material, the spaces which are intended to be hollow. The model may be reproduced in wax by casting in a rubber mold. The wax shape then is placed inside the piston mold 82 before casting. The wax shape is removed from the finished piston by melting. As another alternative, the castings of the pistons can be made with epoxy with glass microsphere filler, a material in general use in automotive body work. The same material may be suitable for making the negative molds 82. This material may be inert enough and its surface roughened, say by sandblasting, to hold a bio-coating as described below.

The preferred machine 10 as a heart pump will now be described with even greater specificity. National Heart, Lung, and Blood Institute (NHLBI) criteria for artificial hearts require an output of 10 liters per minute at $\leq 120$ pulses/min., that is $\geq 83$ cm$^3$/pulse, against a pressure differential of $\Delta P \approx 120$ mmHg = 16 kPa for the left ventricle. For the right ventricle, the same volume requirement exists, but with $\Delta P \approx 20$ mmHg only. The preferred embodiment is designed to pump 100 cm$^3$/pulse. For each full rotation of all the pistons 19 and 20 in the machine 10, there are eight pulses, and therefore a total output per rotation of $V_{out} = 800$ cm$^3$. The total displacement per one rotation of the pump is around 120% of the volume $V_{sp} = 4/3\pi R^3$, where R is the inside radius of the outer shell 14. Solving the equation, $R = (3/4\pi V_{out})^{1/3}$, $R = 54.2$ mm $= 2\frac{1}{8}$". If an r of 54 mm is chosen, the inside diameter of the outer shell 14 therefore equals 108 mm = 4¼", and $V_{sp} = 658.6$ cm$^3$. Therefore $V_{out} = 790.4$ cm$^3$ = 98.8 cm$^3$/pulse, which is close to the desired 100 cm$^3$/pulse. For the inner shell 22, an outside diameter of 38 mm = 1½" is chosen. Note that the sizes of the inner and outer shells 14 and 22 do not affect the shape of the oval conical side surface 26 of the pistons 19 and 20. The shape of the oval conical side surfaces 26 of the pistons 19 and 20 is determined by angular relations alone which are independent of the actual size of the machine 10. The machine 10 as embodied in a heart pump has four different types of surfaces:

1. Interior surfaces not in contact with body fluids. These surfaces include the inside of the equatorial piston cavities 56 and the inside of the inner shell 22.
2. Surfaces in contact with the body external to the cardio-vascular system. This includes the outside surface of the entire machine 10.
3. Surfaces in contact with flowing blood, but otherwise passive. These include the inlet passages 62 and outlet passages 63, and the inner surfaces of the outer connections 70 shown in FIG. 6.
4. Surfaces in contact with flowing blood, "wiping" against each other. These surfaces include interior surfaces of the displacement chambers 25 such as the oval conical side surfaces 26 of the pistons 19 and 20, the substantially spherical outer surface 23 of the inner shell 22, and the substantially spherical interior surface 15 of the outer shell 14.

The surfaces listed under 2, 3, and 4 above should be coated with a biocompatible material such as polyester-polyurethaneurea (PEUU) or other similar materials. This coating of biocompatible material is called a "bio-coating". The surfaces listed under items 3 and 4 above which are in contact with flowing blood may have additional coatings. One coating may be a layer of protein, while a second may be a layer of red blood cells (Thrombus) and fibrin. This double layer is called an Endothelial lining or the Intima. The Intima is formed by the blood itself. The bio-coating must encourage, or at least must not discourage the formation and proper function of the Intima. The bio-coating should provide a suitable mechanical anchoring for the Intima. Teflon, for example, is poor in this respect. A porous surface layer would be good. If the Thrombus were to break off, there would be a danger of embolization. Major factors to be considered in the choice of materials from which to make the pump parts include the ease of manufacturing, and also the application and adherence of the bio-coating.

In the pump the bio-layer, which includes both the bio-coating and the Intima, may have a thickness in the order of 100 microns (micrometers). This thickness should be determined quite precisely for proper functioning of the heart pump. The Intima may have a thickness of 10–30 microns, not including the surface roughness of the bio-coating which may easily be 50 microns deep. In the formation of various machine parts, therefore, an allowance must be made for the bio-layer.

Blood is a composite fluid which has a complex rheology. Its two main components include plasma, which is a low viscosity fluid, and red blood cells. Each red blood cell consists of hemoglobin enclosed in an elastic membrane. When not otherwise constrained, red blood cells have the shape of a round platelet 8.5 microns in diameter and 2.5 microns thick at the edges with a thinner center.

The approximate volume of a red blood cell is 90 cubic microns and the surface area is approximately 160 square microns. Red blood cells readily deform and can pass through openings as small as 0.5 microns wide. If they adhere to a surface, they do so by means of a small appendage and have an appearance like balloons tethered on a short string.

Hemoglobin has a viscosity of $\eta = 6$ centipoise (cp), while the viscosity of plasma is 5 times lower ($\eta = 1.2$ cp). Turbulence sets in at a critical Reynolds number of about 1000. The Reynolds number $= Rv\delta/\eta$, where R is the characteristic radius, and $R \approx \sqrt{A/\pi}$ where A is the cross sectional area of the passage in which the fluid moves.

The problems related to fluid dynamics in working with blood include the following:
1. Hemolysis, which is destruction of the red blood cells.
2. Thromboembolism, the formation of loose blood clots.
3. Tissue overgrowth which includes fibrin growth, and the narrowing of passages ("stenosis").
4. Damage to endothelial tissue lining such as mechanical damage and breaking away from the supporting surfaces.

Shear stresses in the fluid near walls past which the fluid moves may cause a susceptibility to any of these four problems. Too high a shear stress near a wall can cause damage to the red blood cells which form the Intima. Additionally, too high a shear stress near the wall can cause the thrombic material and endothelial tissue to be torn away. Too low a shear stress near the wall encourages thrombus formation and tissue growth. There is no agreement as to the values of "too high" or "too low" but many authors consider greater than 400 dynes/cm$^2$ too high and less than 100 dynes/cm$^2$ as too low. On the whole, one should avoid the creation of regions of flow stagnation and regions of excessive turbulence. As a practical matter, ducts with sharp corners should be avoided. Additionally, shear stresses within bulk flow areas can lead to hemolysis, but the critical values are much higher (approximately > 1500 dynes/cm$^2$).

In the machine 10 applied as a heart pump, the speed of the ends 32 of the pistons 19 and 20 is about 25 cm/sec. at 120 pulse/min. (0.5 rps). Assuming a "(d)" separation between individual pistons 19 and 20, between the spherical outer surface 23 of the inner shell 22 and the bottom surface 31 of the pistons 19 and 20, and between the spherical interior surface 15 of the outer shell 14 and the top surface 30 of the pistons 19 and 20 of about 30 microns (the distance between surfaces of the Intima), shear stresses $\sigma s \leq (\eta v/d)$ are obtained, with $1.2 < \eta < 6$ cp($1$ cp$= 10^{-3}$Ns/m$^2$). The maxima for $\sigma_s$ lie between 10 and 50 Pa (10 Pa = 100 dynes/cm$^2$). A distance between the conical side surfaces 26 of the individual pistons 19 and 20, and between the pistons 19 and 20 inner and outer spheres 14 and 22 of approximately 80 microns from bio-coating surface (porous or not) to bio-coating surface is suggested. The purpose of this distance is to accommodate two Endothelial linings of 20±10 microns each and a gap of 40 ±10 microns. A machining tolerance of the bio-coated parts of ±20 microns might be acceptable.

The pistons 19 and 20 preferably should be formed of a casting compound. The inner and outer shells 14 and 22 are preferably formed out of a metal which is easy to machine, and is stronger than the casting compound, and yet which is compatible with the preferred bio-coating. For example, brass and stainless aluminum alloys might be used. Nevertheless, the inner and outer shells 14 and 22 might also be cast. For strength, epoxy with a glass fiber reinforcement in the shells 14 and 22 may be utilized.

As the connections 70 are attached to the appropriate arteries and veins, the machine 10 is filled with blood in spaces within the machine 10. The machine 10 then may be operated by directing electrical current to the four motors 55 within the cavities 56 in the equatorial pistons 19. As the motors 55 operate, the small gears 57 rotate and cause the equatorial pistons 19 to be rotated through the spur gears 59 and inside ring gears 60.

The rotation of the equatorial pistons 19 causes a simultaneous rotation of the four attached piston gears 40, which in turn drive the eight connecting gears 41. The connecting gears 41 drive the two piston gears 40 attached to the polar pistons 20, and ensure that all of the pistons 19 and 20 rotate at the same angular velocity and direction with respect to the center of the interior of the machine 10.

As the pistons 19 and 20 rotate the displacement chambers 25 change in size so as to open and close. As a chamber 25 expands, blood is drawn into the chamber 25 through the adjoining inlet passage 62. Blood flows into the polar piston 20 through the inlet orifice 11, and out into the displacement chamber 25 through a pair of inlet apertures 65 which open into the chamber 25 when it is expanding. When the chamber 25 is contracting, a pair of outlet apertures 66 instead open into the chamber 25. As the chamber 25 contracts, blood flows into the outlet passage 63 through the pair of outlet apertures 66, and then out of the piston 20 and machine 10 through the outlet orifice 12.

Blood which flows into the lower half of the machine 10 is not normally mixed within the machine 10 with blood in the upper half of the machine 10. Therefore, the machine 10 can operate in a similar manner as does the human heart, which actually is a double pump pumping blood both into the heart and into the body.

Although the machine 10 as disclosed in FIGS. 1–12 and 15–16 is a heart alternatively the machine 10 can serve as some other type of pump, as a compressor or as an internal combustion engine. The technology to modify the machine 10 into an internal combustion engine is well known in the art. The displacement chambers 25 become combustion chambers. In such an embodiment, the pistons 19 and 20 are made from metal or other material which would be able to withstand the combustion. The machine 10 also include means for igniting the combustibles within each of the chambers, such as spark plugs. The positions of the apertures 65 and 66 may be changed to allow for timely intake of fuel and discharge of combustion byproducts, so that the polar pistons function properly as valves. In its embodiment as an engine, the spherical rotary machine may preferably have gearing external to the outer shell, which causes the pistons to rotate in synchrony at identical speed and direction with respect to the machine center. The machine 10 as an engine could operate somewhat similarly to Wankel engines, which are quite well known in the art of internal combustion engines.

It is understood that the invention is not confined to the particular construction and arrangement herein illustrated and described, but embraces such modified forms thereof as come within the scope of the following claims.

What is claimed is:

1. A spherical rotary machine comprising:
   (a) an outer shell including a substantially spherical interior surface forming an interior with a center; and
   (b) six rotary pistons within the interior of the outer shell which are each rotatable about its own central axis, the six axes being orthogonally centered on the center of the interior of the outer shell, each piston including a top convex spherical surface conforming substantially in shape to and located adjacent to the spherical interior surface, and an oval conical side surface substantially defined by line segments which are substantially radial with respect to a point near the center, the oval side surface of each piston at least nearly touching tangentially along generally radial line segments the oval side surface of each of its four adjacent pistons as the six pistons rotate, so that the oval side surfaces of any three adjacent pistons form a displacement chamber which varies in size as the pistons rotate.

2. The spherical rotary machine of claim 1 wherein the generally radial line segments where three adjacent pistons at least nearly touch define, on the oval conical side surfaces of the three pistons, substantially identical portions which change in size with piston rotation, and wherein the displacement chambers are each centered equidistant from the axes of the three adjacent pistons.

3. The spherical rotary machine of claim 1 further comprising means for causing the pistons to rotate at identical angular velocities and directions with respect to the center of the interior of the outer shell.

4. The spherical rotary machine of claim 1 further comprising: a central core centered within the interior of the outer shell; and six piston shafts which each extend from the central core into a bearing hole in a truncated bottom surface of one piston in coaxial relation tot he piston central axis.

5. The spherical rotary machine of claim 4 further comprising: at least three piston gears, each piston gear coaxially connected to the truncated bottom surface of one piston to rotate with the piston; and at least one connecting gear positioned between three adjacent piston gears and operably connected thereto, so that rotation of any one piston causes simultaneous rotation of at least two other pistons.

6. The spherical rotary machine of claim 1 further comprising: an inner shell including a substantially spherical outer surface thereon centered on the center of the interior of the outer shell, wherein each piston includes a bottom concave spherical surface conforming substantially in shape to and located adjacent to the spherical outer surface of the inner shell, truncating the oval conical side surface.

7. The spherical rotary machine of claim 6 wherein the inner shell has six openings, each aligned with one piston axis, and the machine further includes six piston gears, each piston gear coaxially connected to the bottom surface of one piston and extending through one opening into the inner shell; a central core which is centered within the interior of the outer shell and the inner shell; six piston axles which each extend from the central core into a bearing hole in one piston gear and piston in coaxial relation to the piston central axis; and eight connecting gears, each connecting gear rotatably mounted between the central core and inner shell and between and operably connected to three adjacent piston gears so that rotation of any piston causes rotation of all pistons.

8. The spherical rotary machine of claim 7 wherein the piston gears and connecting gears are bevel gears which are beveled at an angle of about 27.3678° to their axes.

9. The spherical rotary machine of claim 1 wherein the oval conical side surface of each piston includes two piston ends which are about 180° apart with respect to the central axis and are each inclined at approximately a 54.7356° angle to the central axis of the piston, and wherein the oval conical surface at about 90° from either end with respect to the central axis is inclined at approximately a 35.2644° angle to the central axis of the piston.

10. The spherical rotary machine of claim 9 wherein the oval conical side surface of each piston includes two opposed elliptical conical surface sections which are each centered at about 90° from both ends with respect to the central axis.

11. The spherical rotary machine of claim 10 wherein the two opposed elliptical conical surface sections extend to and intersect at each piston end along a line which is inclined at approximately a 54.7356° angle to the central axis of the piston.

12. The spherical rotary machine of claim 10 wherein the oval conical side surface of each piston further includes two cylindrical surface sections at the ends of the piston which intersect the two opposed elliptical conical surface sections which extend between the cylindrical surface sections.

13. The spherical rotary machine of claim 12 wherein the two cylindrical surface sections of each piston at least nearly touch only the elliptical conical surface sections of other pistons as the pistons rotate.

14. The spherical rotary machine of claim 3 wherein four of said rotary pistons are equatorial pistons having coplanar central axes, each equatorial piston having a cavity extending radially inwardly from a top of the piston and formed concentric to the central axis of the piston; and
   wherein the machine further includes: a motor for each equatorial piston substantially located within the cavity and mounted to the outer shell, and means for directing rotational motion from each motor to the adjacent piston.

15. The spherical rotary machine of claim 14 wherein the spherical interior surface of the outer shell defines an access opening for each equatorial piston located radially outward from the piston cavity with respect to the center of the interior; and wherein the outer shell further includes a piston cover for each equatorial piston which each is positioned' to cover and close one access opening and cavity.

16. The spherical rotary machine of claim 15 wherein the rotational motion directing means for each piston comprises a small gear on a shaft of the motor, at least one spur gear pivotally mounted to the adjacent piston cover and operably connected to the small gear, and an inside ring gear positioned along a periphery of the piston cavity and which is operably connected to the spur gears so that rotation of the motor shaft causes rotation of the piston.

17. The spherical rotary machine of claim 10 wherein fewer than three of said rotary pistons are polar pistons having coaxial central axes, each polar piston having therein an inlet passage forming an inlet orifice in the top convex spherical surface of the piston and a set of inlet apertures opening near one end of each elliptical conical surface section such that as the piston rotates, each inlet aperture lags with respect to the adjacent piston end.

18. The spherical rotary machine of claim 10 wherein fewer than three of said rotary pistons are polar pistons having coaxial central axes, each polar piston having therein an outlet passage forming an outlet orifice in the top convex spherical surface of the piston and a set of outlet apertures opening near one end of each elliptical conical surface section such that as the piston rotates, each outlet aperture leads with respect to the adjacent end.

19. A heart pump machine comprising:
   (a) an outer shell including a substantially spherical interior surface forming an interior with a center and at least one fluid transfer opening; and
   (b) six rotary pistons within the interior of the outer shell which are each rotatable about its own central axis, the six axes being orthogonally centered on the center of the interior of the outer shell, each piston including a top convex spherical surface conforming substantially in shape to and located adjacent to the spherical interior surface, an oval conical side surface substantially defined by line segments which are radial with respect to the center and including two piston ends which are about 180° apart with respect to the central axis and two opposed elliptical conical surface sections which are each centered at about 90° from both ends with respect to the central axis, the oval side surface of each piston at least nearly touching tangentially along generally radial line segments the oval side surface of each of its four adjacent pistons as the six pistons rotate, so that the oval side surfaces of any three adjacent pistons form a displacement chamber which varies in size as the pistons rotate, two of said pistons which have coaxial central axes being polar pistons which each has an inlet passage therein forming an inlet orifice in the top convex spherical surface of the polar piston and a set of inlet apertures opening near one end of each elliptical conical surface section such that as the piston rotates, each inlet aperture lags with respect to the adjacent end, and each polar piston also has therein an outlet passage forming an outlet orifice in the top convex spherical surface of the piston and a set of outlet apertures opening near one end of each elliptical conical surface section such that as the piston rotates, each outlet aperture leads with respect to the adjacent piston end, each inlet and outlet orifice opening through one of the fluid transfer openings in the outer shell.

20. The heart pump machine of claim 19 further comprising means for causing the pistons to rotate at identical angular velocities and directions with respect to the center of the interior of the outer shell.

21. The heart pump machine of claim 19 including an inner shell having a substantially spherical outer surface centered on the center of the interior of the outer shell, wherein the inner shell has six openings, each aligned with one piston axis, and the machine further includes six piston gears, each piston gear coaxially connected to the bottom surface of one piston and extending through one opening into the inner shell; a central core which is centered within the interior of the outer shell and the inner shell; six piston axles which each extend from the central core into a bearing hole in one piston gear and piston in coaxial relation to the piston central axis; and eight connecting gears, each connecting gear rotatably mounted between the central core and inner shell and between and operably connected to three adjacent piston gears so that rotation of any piston causes rotation of all pistons.

22. The heart pump machine of claim 19 wherein the two piston ends are each inclined at approximately a 54.7356° angle to the central axis of the piston, and the oval conical surface at about 90° from either end with respect to the central axis is inclined at approximately a 35.2644° angle to the central axis of the piston.

23. The heart pump machine of claim 22 wherein the two opposed elliptical conical surface sections extend to and intersect at each piston end along a line which is inclined at approximately a 54.7356° angle to the central axis of the piston.

24. The heart pump machine of claim 22 wherein the oval conical side surface of each piston further includes two cylindrical surface sections at the ends of the piston which intersect the two opposed elliptical conical surface sections which extend between the cylindrical surface sections.

25. The heart pump machine of claim 20 wherein four of said rotary pistons are equatorial pistons having coplanar central axes, each equatorial piston having a cavity extending radially inwardly from a top of the piston and formed concentric to the central axis of the piston; and
   wherein the machine further includes a motor for each equatorial piston substantially located within the cavity and mounted to the outer shell, and means for directing rotational motion from each motor to the adjacent piston.

26. A spherical rotary machine comprising:
   (a) an outer shell including a substantially spherical interior surface forming an interior with a center;
   (b) six rotary pistons within the interior of the outer shell which are each rotatable about its own central axis, the six axes being orthogonally centered on the center of the interior of the outer shell, each piston including a top convex spherical surface conforming substantially in shape to, and located adjacent to the spherical interior surface, and an oval conical side surface substantially defined by line segments which are radial with respect to the center, the oval side surface of each piston at least nearly touching tangentially along generally radial line segments the oval side surface of each of its four adjacent pistons as the six pistons rotate, so that the oval side surfaces of any three adjacent pistons form a displacement chamber which varies in size as the pistons rotate;
   (c) a central core centered within the interior;
   (d) six piston shafts which each extend from the central core into a bearing hole in a truncated bottom surface of one piston in coaxial relation to the piston central axis;
   (e) one piston gear for each piston, each piston gear coaxially connected to the truncated bottom surface of one piston to rotate with the piston; and
   (f) at least one connecting gear positioned between three adjacent piston gears and operably connected thereto, so that rotation of any one piston causes simultaneous rotation of at least two other pistons.

27. The spherical rotary machine of claim 26 further comprising an inner shell including a substantially spherical outer surface thereon centered on the center of the interior of the outer shell, the inner shell also having six openings through which each of the piston gears extend into the inner shell; wherein each piston includes a bottom concave spherical surface conforming substantially in shape to and located adjacent to the spherical outer surface' of the inner shell, truncating the oval conical side surface and thereby forming said truncated bottom surface of the piston; and wherein each connecting gear is rotatably mounted between the central core and inner shell and between and operably connected to three adjacent piston gears so that rotation of any piston causes rotation of all pistons.

28. The spherical rotary machine of claim 26 wherein the oval conical side surface of each piston includes two piston ends which are about 180° apart with respect to the central axis and are each inclined at approximately a 54.7356° angle to the central axis of the piston, and wherein the oval conical surface at about 90° from either end with respect to the central axis is inclined at approximately a 35.2644° angle to the central axis of the piston.

29. The spherical rotary machine of claim 28 wherein the oval conical side surface of each piston includes two opposed elliptical conical surface sections which are each centered at about 90° from both ends with respect to the central axis.

30. The spherical rotary machine of claim 29 wherein the two opposed elliptical conical surface sections extend to and intersect at each piston end along a line which is inclined at approximately a 54.7356° angle to the central axis of the piston.

31. The spherical rotary machine of claim 29 wherein the oval conical side surface of each piston further includes two cylindrical surface sections at the ends of the piston which intersect the two opposed elliptical conical surface sections which extend between the cylindrical surface sections.

32. The spherical rotary machine of claim 26 wherein four of said rotary pistons are equatorial pistons having coplanar central axes, each equatorial piston having a cavity extending radially inwardly from a top of the piston and formed concentric to the central axis of the piston; and
wherein the machine further includes: a motor for each equatorial piston substantially located within the cavity and mounted to the outer shell, and means for directing rotational motion from each motor to the adjacent piston.

33. The spherical rotary machine of claim 29 wherein fewer than three of said rotary pistons are polar pistons having coaxial central axes, each polar piston having therein an inlet passage forming an inlet orifice in the top convex spherical surface of the piston and a set of inlet apertures opening near one end of each elliptical conical surface section such that as the piston rotates, each inlet aperture lags with respect to the adjacent piston end.

34. The spherical rotary machine of claim 29 wherein fewer than three of said rotary pistons are polar pistons having coaxial central axes, each polar piston having therein an outlet passage forming an outlet orifice in the top convex spherical surface of the piston and a set of outlet apertures opening near one end of each elliptical conical surface section such that as the piston rotates, each outlet aperture leads with respect to the adjacent end.

35. A spherical rotary machine comprising:
(a) an outer shell including a substantially spherical interior surface forming an interior with a center;
(b) six rotary pistons within the interior of the outer shell which are each rotatable about its own central axis, the six axes being orthogonally centered on the center of the interior of the outer shell, each piston including a top convex spherical surface conforming substantially in shape to and located adjacent to the spherical interior surface, and an oval conical side surface substantially defined by line segments which are radial with respect to the center, the oval side surface of each piston at least nearly touching tangentially along generally radial line segments the oval side surface of each of its four adjacent pistons as the six pistons rotate, so that the oval side surfaces of any three adjacent pistons form a displacement chamber which varies in size as the pistons rotate; and
(c) gear means for interlocking the pistons to rotate synchronously at identical angular velocity and direction with respect to the center of the interior of the outer shell.

36. The spherical rotary machine of claim 35 further comprising: a central core centered within the interior of the outer shell; and six piston shafts which each extend from the central core into a bearing hole in a truncated bottom surface of one piston in coaxial relation to the piston central axis.

37. The spherical rotary machine of claim 36 wherein the gear means comprises: one piston gear for each piston, each piston' gear coaxially connected to the truncated bottom surface of one piston to rotate with the piston; and eight connecting gears, one connecting gear positioned between each three adjacent piston gears and operably connected thereto, so that rotation of any one piston causes simultaneous rotation of all other pistons.

38. The spherical rotary machine of claim 37 further comprising: an inner shell including a substantially spherical outer surface thereon centered on the center of the interior of the outer shell, the inner shell also having six openings through which each of the piston gears extends into the inner shell; wherein each piston includes a bottom concave spherical surface conforming substantially in shape to and located adjacent to the spherical outer surface of the inner shell, truncating the oval conical side surface and thereby forming said truncated bottom surface of the piston; and wherein each connecting gear is rotatably mounted between the central core and inner shell.

39. The spherical rotary machine of claim 37 wherein the oval conical side surface of each piston includes two piston ends which are about 180° apart with respect to the central axis and are each inclined at approximately a 54.7356° angle to the central axis of the piston, and wherein the oval conical surface at about 90° from either end with respect to the central axis is inclined at approximately a 35.2644° angle to the central axis of the piston.

40. The spherical rotary machine of claim 39 wherein the oval conical side surface of each piston includes two opposed elliptical conical surface sections which are each centered at about 90° from both ends with respect to the central axis.

41. The spherical rotary machine of claim 40 wherein the two opposed elliptical conical surface sections extend to and intersect at each piston end along a line which is inclined at approximately a 54.7356° angle to the central axis of the piston.

42. The spherical rotary machine of claim 40 wherein the oval conical side surface of each piston further includes two cylindrical surface sections at the ends of the piston which intersect the two opposed elliptical conical surface sections which extend between the cylindrical surface sections.

43. The spherical rotary machine of claim 37 wherein four of said rotary pistons are equatorial pistons having coplanar central axes, each equatorial piston having a cavity extending radially inwardly from a top of the piston and formed concentric to the central axis of the piston; and wherein the machine further includes: a motor for each equatorial piston substantially located within the cavity and mounted to the outer shell, and means for directing rotational motion from each motor to the adjacent piston.

44. The spherical rotary machine of claim 40 wherein fewer than three of said rotary pistons are polar pistons having coaxial central axes, each polar piston having therein an inlet passage forming an inlet orifice in the top convex spherical surface of the piston and a set of inlet apertures opening near one end of each elliptical conical surface section such that as the piston rotates, each inlet aperture lags with respect to the adjacent piston end.

45. The spherical rotary machine of claim 40 wherein fewer than three of said rotary pistons are polar pistons having coaxial central axes, each polar piston having therein an outlet passage forming an outlet orifice in the top convex spherical surface of the piston and a set of outlet apertures opening near one end of each elliptical conical surface section such that as the piston rotates, each outlet aperture leads with respect to the adjacent end.

* * * * *